(12) United States Patent
Esanu

(10) Patent No.: US 9,993,263 B2
(45) Date of Patent: Jun. 12, 2018

(54) METHOD AND DEVICE FOR ULTRASOUND GUIDED MINIMAL INVASIVE ACCESS OF A BODILY CAVITY

(71) Applicant: Catalin Esanu, Horn (AT)

(72) Inventor: Catalin Esanu, Horn (AT)

( * ) Notice: Subject to any disclaimer, the term of this patent is extended or adjusted under 35 U.S.C. 154(b) by 349 days.

(21) Appl. No.: 14/568,198

(22) Filed: Dec. 12, 2014

(65) Prior Publication Data

US 2015/0327885 A1 Nov. 19, 2015

Related U.S. Application Data

(60) Provisional application No. 61/914,997, filed on Dec. 12, 2013.

(51) Int. Cl.

| | | |
|---|---|---|
| A61B 1/32 | (2006.01) |
| A61B 17/34 | (2006.01) |
| A61B 17/02 | (2006.01) |
| A61M 29/02 | (2006.01) |
| A61M 25/10 | (2013.01) |
| A61B 17/32 | (2006.01) |
| A61B 17/42 | (2006.01) |
| A61B 17/00 | (2006.01) |
| A61B 90/00 | (2016.01) |

(52) U.S. Cl.
CPC ...... *A61B 17/3403* (2013.01); *A61B 17/0281* (2013.01); *A61B 17/3417* (2013.01); *A61B 17/3439* (2013.01); *A61B 17/3474* (2013.01); *A61B 17/42* (2013.01); *A61B 2017/00115* (2013.01); *A61B 2017/00199* (2013.01); *A61B 2017/00557* (2013.01); *A61B 2017/320048* (2013.01); *A61B 2017/3413* (2013.01); *A61B 2017/3454* (2013.01); *A61B 2017/3486* (2013.01); *A61B 2017/3488* (2013.01); *A61B 2017/4225* (2013.01); *A61B 2090/378* (2016.02); *A61M 25/10182* (2013.11); *A61M 29/02* (2013.01); *A61M 2029/025* (2013.01)

(58) Field of Classification Search
CPC . A61B 17/34; A61B 17/0281; A61B 17/3403; A61B 2090/3782; A61B 2090/3784; A61B 2017/3413; A61B 2017/3486; A61B 2017/4225
USPC .......................................................... 600/207
See application file for complete search history.

(56) References Cited

U.S. PATENT DOCUMENTS 5,209,721 A 5/1993 Wilk
6,156,006 A * 12/2000 Brosens ........... A61B 17/00234
604/104

(Continued)

*Primary Examiner* — Kristen Matter

(57) ABSTRACT

A puncture assistance device for use in connection with an ultrasound probe to guide a Veress needle through the layers of the wall into a bodily cavity is provided. The puncture assistance device comprises a tenaculum-like forceps, a needle guide body provided with a slot for guiding the Veress needle within the scan plane of the ultrasound probe, attachment means to the ultrasound probe, and attachment means of the needle guide to the tenaculum-like forceps. Also provided is a balloon catheter for use as a retractor in gaining access into the abdominal cavity, presenting at its distal end an inflatable balloon membrane and an framework of non-distendable flexible fibers disposed in a specific arrangement. A method access the abdominal cavity with the aid of said devices under ultrasound guidance is also provided.

8 Claims, 12 Drawing Sheets

(56) References Cited

U.S. PATENT DOCUMENTS

| | | | |
|---|---|---|---|
| 6,293,952 B1 * | 9/2001 | Brosens | A61B 17/00234 604/164.01 |
| 7,507,209 B2 | 3/2009 | Nezhat | |
| 7,918,795 B2 | 4/2011 | Grossman | |
| 2003/0163142 A1 * | 8/2003 | Paltieli | A61B 17/3403 606/130 |
| 2005/0131291 A1 * | 6/2005 | Floyd | A61B 17/3403 600/424 |
| 2006/0241651 A1 * | 10/2006 | Wilk | A61B 17/3423 606/108 |
| 2007/0167808 A1 * | 7/2007 | Nozaki | A61B 8/0833 600/459 |
| 2010/0106056 A1 * | 4/2010 | Norris | A61B 8/0841 600/567 |
| 2012/0245510 A1 | 9/2012 | Rakower | |
| 2012/0253297 A1 | 10/2012 | Matsunawa | |
| 2016/0008075 A1 * | 1/2016 | Velhamos | A61M 13/003 600/464 |
| 2016/0302825 A1 * | 10/2016 | Arts | A61B 10/06 |

* cited by examiner

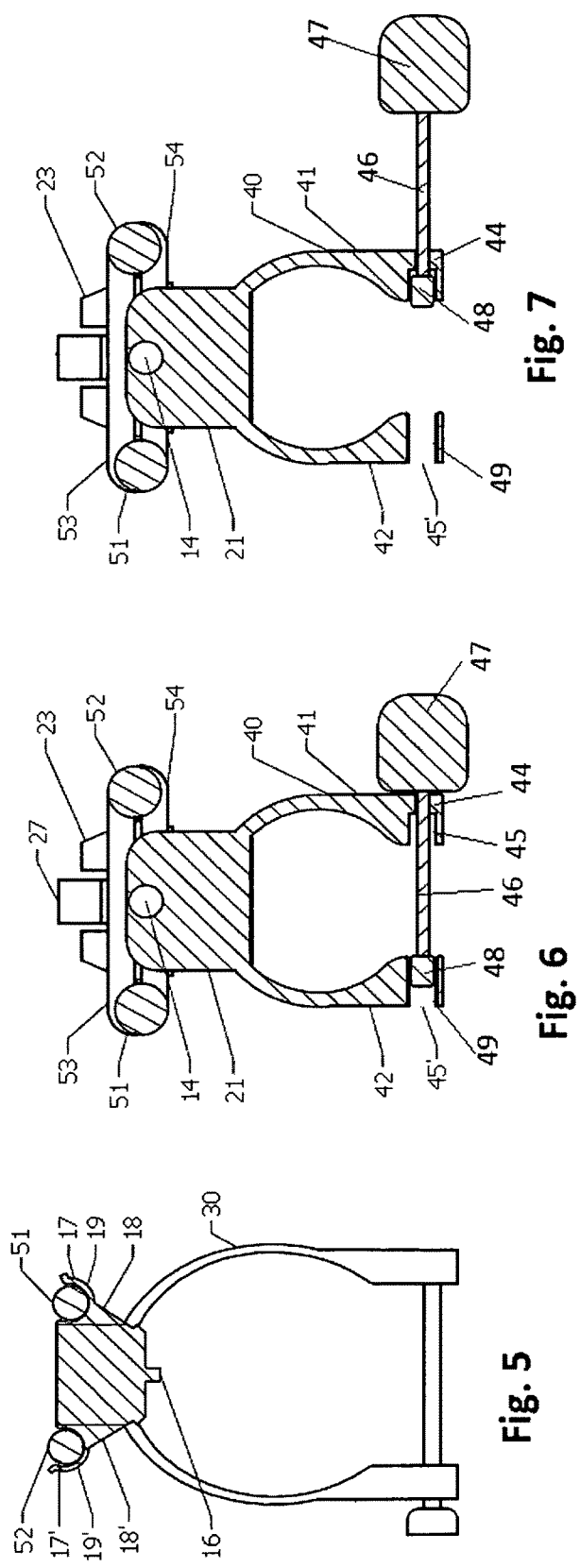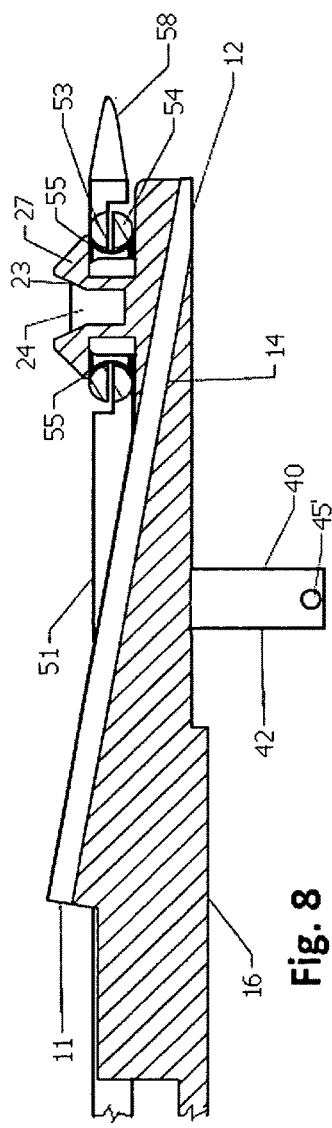

METHOD AND DEVICE FOR ULTRASOUND GUIDED MINIMAL INVASIVE ACCESS OF A BODILY CAVITY

BACKGROUND OF THE INVENTION

Over the past 50 years, developments in electronic and optical technologies have meant that it has become possible to perform many operations laparoscopically. The unique feature distinguishing laparoscopic from open abdominal or vaginal surgery is the need to insert needles, trocars and cannulas for initial entry into the abdomen, the insertion of the primary trocar being made blindly in most cases. This may result in inadvertent bowel or vascular injury which can be responsible for major morbidity and mortality. In the last 25 years great efforts have been made for the prevention of these injuries by developing so called safe entry techniques especially because almost 75% of the complications of laparoscopic surgery occur at the time of primary entry site into the abdomen, before even surgery has begun.

The classic site for gaining access into the abdominal cavity by insertion of the first trocar is the umbilicus, this being the thinnest part of the abdominal wall, with abdominal fasciae fused into the umbilical ring.

The problem resides in the proximity of the large retroperitoneal vessels and the frequency of infraumbilical adhesions by the bowel and omentum found in almost 10% of cases, which can lead to injury of the aforementioned structures, especially in the case of a previous laparotomy or obese or too thin patients.

The closed entry technique comprises the Veress needle technique and the direct entry technique. The technique used by most gynecologic surgeons implies inserting a hollow needle called the Veress needle into the abdomen through the abdominal wall, after lifting the latter, performing a series of tests that whiteness the probable location of the tip inside the abdomen, insufflation of the abdomen with $CO_2$ to a predetermined set pressure and insertion of a trocar cannula after the removal of the needle. Note that there are three blind steps in performing this procedure: insertion of the Veress needle, insufflation and insertion of the cannula. The direct trocar entry implies insertion of the primary trocar through the umbilicus, followed by insertion of the optics and the insufflation of the abdominal cavity. Although it takes less time to perform than the Veress needle technique, and is associated with less minor insufflation-related side effects, the possible complications associated with insertion of a large sharp instrument blindly could prove to be severe.

The open Hasson technique (U.S. Pat. No. 3,817,251) implies the visualization and cutting of the abdominal layers upon entry by using blunt and sharp dissection, and insertion of the primary trocar under sight. This technique has not lowered the rate of bowel complications however in large population studies, just the recognition of them.

The radially expanding access system (U.S. Pat. No. 5,827,319), was developed to minimize tissue trauma. This system uses a pneumoperitoneum needle with a polymeric sleeve. Following routine insufflation the needle is removed leaving the outer sleeve in situ, followed by direct dilatation of the sleeve into creation of a port. Complications are similar to the ones of the closed technique.

Visual trocars imply the use of optics through the cannulas upon insertion through the abdominal layers (U.S. Pat. No. 6,638,265, States Surgical Corps Visiport™ trocar and the Ethicon Endosurgery's Optiview™). Studies have not shown a reduction of entry complication by using these techniques, but only the rate of recognition.

However, the incidence of first entry complications remains the same in the last 25 years, whichever technique is performed, in spite of the technical progress, studies not showing the superiority of either technique into lowering the complication rate.

Attempts to use ultrasound as a recognition tool for umbilical adhesions have been made. The "Visceral slide" technique developed by F. Tu et al. uses an abdominal probe placed over the umbilicus and the patient is asked to take very quick and large breaths. The underlying viscera (bowel) move freely relative to the abdominal wall for 3-5 in normal cases. In the event of underlying adhesions, there is no or little movement.

The PUGSI technique (Peroperative periumbilical ultrasound-guided saline infusion) developed by C. Nezhat et al. implies performing visceral slide followed by infraumbilical injection of 6-10 cc of sterile saline through a spinal needle under direct ultrasound guidance. Formation of fluid pocket and non-dispersion suggest subumbilical adhesions.

U.S. Pat. No. 5,209,721 uses a Veress needle with an ultrasonic wave generator and a sensor mounted thereon, monitoring ultrasonic pressure waves reflected from internal organs or tissues located along the insertion path of the needle.

Various designs of percutaneous needle guides for attachment to non-invasive medical scanning devices, for example hand-held transducer probes, are known in the art. These guides may be used to direct a percutaneous needle to a needle entry site, which is located alongside the scanning device on an epidermis of a scanned body, and which corresponds to a subcutaneous target located by the device.

SUMMARY OF THE INVENTION

In accordance with the present invention, a puncture assistance device for use in connection with an ultrasound probe to guide a Veress needle through the layers of the abdominal wall into the abdominal cavity is provided. The puncture assistance device comprises a tenaculum-like forceps provided with ratchet fixation and sharp incurving, needle like pointed blades, a needle guide body provided with a slot for guiding the Veress needle within the scan plane of the ultrasound probe, attachment means by clamp locking mechanism to the ultrasound probe, and attachment means of the needle guide to the tenaculum-like forceps. The improvement consists in the possibility of maneuvering the abdominal layers by the tenaculum-like forceps, into spacing them apart for better ultrasound view and to create access space between inner organs and the abdominal wall for preventing entry injuries.

Pursuant to another feature of the present invention, a balloon catheter for use as a retractor in gaining access into the abdominal cavity, is comprising a double lumen elongated shaft with a first lumen through which the Veress needle is inserted, a cylindrical balloon retractor that is attached on the outer surface of the elongated shaft, providing an inner balloon membrane that is inflatable to a maximum volume and an attached outer framework of non-distendable flexible fibers disposed in a specific arrangement on the different faces of the balloon. The fibers are having a cobweb-like structure associated with radially ascending fibers from the outer edge of the cobweb like mesh to the elongated shaft on the upper surface of cylindrical balloon, a continuous non-pierceable membrane on the lower face, and interconnecting fibers between the two faces. A pilot balloon made of expandable material with a rigid frame that is provided with a female syringe connector with a one way valve and tubing with reinforcement for connection to the cylindrical balloon retractor through the second lumen of the elongated shaft. The balloon retractor is inserted as an external sheet of the Veress needle through the layers of the abdomen with balloon in a collapsed state, followed by its inflation, and upon piercing by a sharp trocar through the layers of the abdomen and balloon, the burst of said balloon is followed by the entanglement of the tip of the trocar in said cobweb-like mesh and impaction in said inferior membrane, preventing thereby puncturing wounds to the internal organs made by the sharp tip of the trocar upon insertion.

Another aspect of the current invention is represented by a method to develop pneumoperitoneum with the aid of an ultrasound device. This is comprising making an incision in the skin of the abdominal wall, attaching the puncturing assistance device that is operatively connected to an ultrasound transducer to the abdominal fascia, inserting a Veress needle through the said puncturing device, observing the path of the Veress needle through the layers of the abdomen by means of the ultrasound transducer that sends an image to a ultrasound monitor, interpreting the image by the operator and redirecting the needle according to the information until entering the peritoneum, insufflating the abdominal cavity while observing with the ultrasound transducer. A safety alternative is represented by the use of the balloon retractor that is used as a sheet of the Veress needle upon insertion, and by inflation protects the content of the abdomen from piercing injuries made by the tip of the trocar.

Advantages of the current invention include, but are not limited to:
- Any point on the abdominal wall can be point of first entry, regardless of the BMI of the patient, location and size of prior laparotomies, the entries of the following trocars being made under sight
- Transforms the blind gestures of first entry into standard, reproducible and documentable ones
- Offers enhanced and "in depth" visualization of the abdominal wall layers and the mobility of the inner organs by applying traction on the abdominal wall,
- Offers the possibility to redirect the Veress needle in a safe area, according to findings by simple tilting of the puncture assistance device, or by removing and reapplying it in the same incision
- Offers enhanced sight in obese patients as the ultrasound probe is applied on the fascial layer
- Use of the balloon retractor protects the inner organs and great vessels from injuries made by the sharp tip of the trocar, and deviates loose adhesions from the path of the trocar
- Can be performed by a single operator, who can also perform intraoperative tests like visceral slide or PUGSI
- In thin patients tests can be made without skin incision, simply by applying the tenaculum on the skin.

DETAILED DESCRIPTION

In the following specification I shall nominate as proximal a part of the assembly that is located relatively close to the operator, and as distal a part of the assembly that is located further away from the operator and hence close to the operating field.

Figure 1:
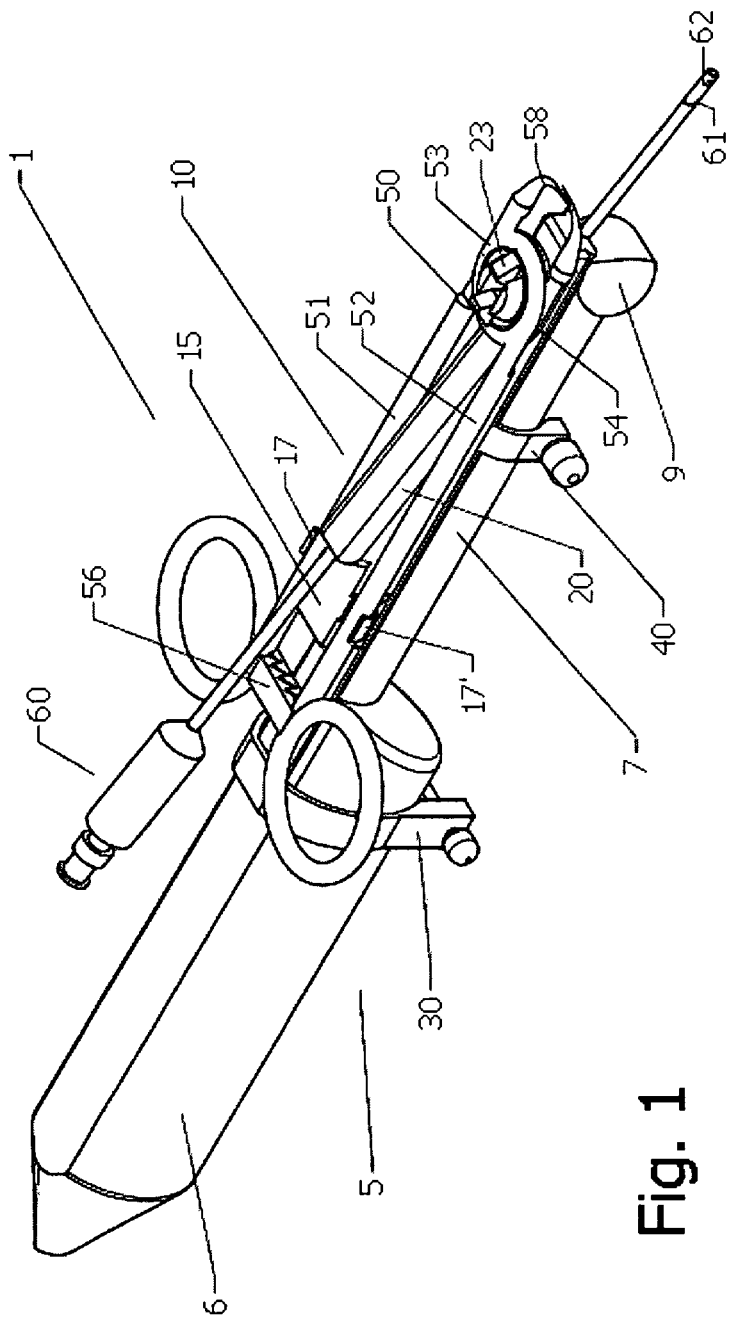
FIG. 1 Isometric right top view of the ultrasound probe—puncture assistance device—Veress needle FIG. 2 Exploded view of the ultrasound probe—puncture assistance device—Veress needle FIG. 3 Isometric left bottom view of the puncture assistance device FIG. 4 Isometric left top view of the puncture assistance device FIG. 5 Sectional transverse front view of the puncture assistance device FIG. 6 Sectional transverse rear view of the puncture assistance device FIG. 7 Sectional transverse rear view of the puncture assistance device FIG. 8 Sectional sagittal view of the puncture assistance device FIG. 9 Isometric bottom view of the balloon retractor and Veress needle FIG. 10 Section view of the pilot balloon FIG. 11 Isometric top view of the balloon retractor and Veress needle FIG. 12 Detailed isometric view of the balloon retractor FIG. 13 Isometric view of the abdominal wall illustrating method of use FIG. 14 Isometric view of the abdominal wall illustrating method of use FIG. 15 Isometric view of the abdominal wall illustrating method of use FIG. 16 Isometric view of the abdominal wall illustrating method of use FIG. 17 Isometric view of the abdominal wall illustrating method of use FIG. 18 Isometric view of an alternate embodiment of the invention
Figure 2:
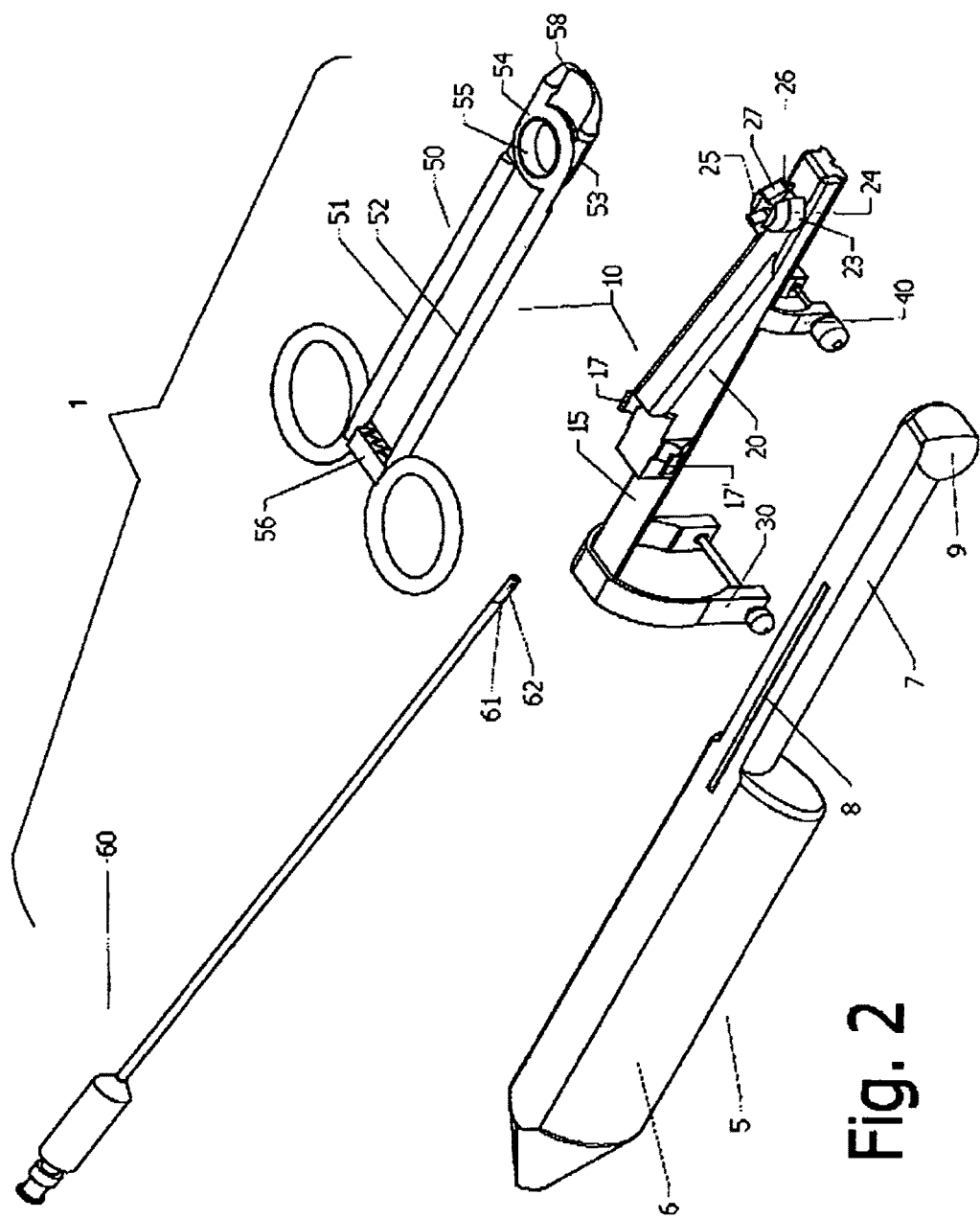

FIG. 1 presents an isometric right top view of the assembly 1, formed by the ultrasound probe 5 in combination with the puncture assistance device 10 to which the Veress needle 60 is added, and FIG. 2 presents an exploded isometric view of the same. They depict an elongated ultrasound probe 5 that is otherwise known to be used for transvaginal or transrectal diagnostic procedures, with a flattened upper surface, formed of an elongated handle part 6 that serves to be gripped by the operator, an elongated shaft 7 that presents an elongated niche 8 on its flattened upper side (FIG. 2), and a rounded distal scanning part 9 that sends and receives ultrasound signals to/from the area to be examined that are converted to an image on the desktop of the ultrasound scanning device, this image serving to be interpreted by the examiner.

The Veress needle 60 depicted in the following is represented by a tubular needle shaft with a needle tip 61 and a tubular obturator that is slidably located inside the needle shaft and has an open front end 62. The obturator has an extended position with its front end in front of the needle tip of the needle shaft and a retracted position with its front end behind the needle tip. The obturator forms a channel there trough to pass an article out the open front end.

Figure 3:
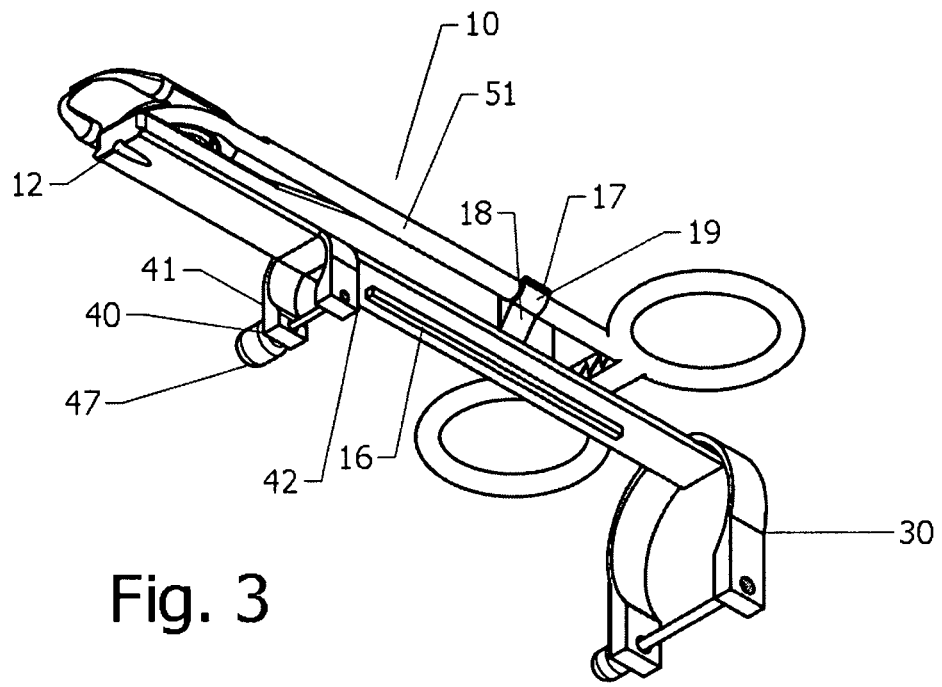
Figure 4:
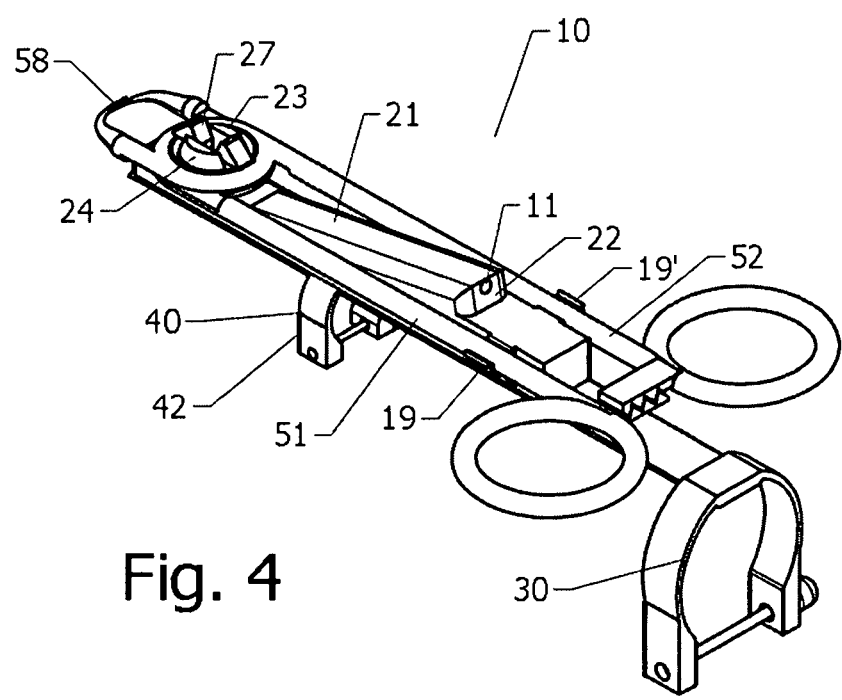
Figures 9, 10:
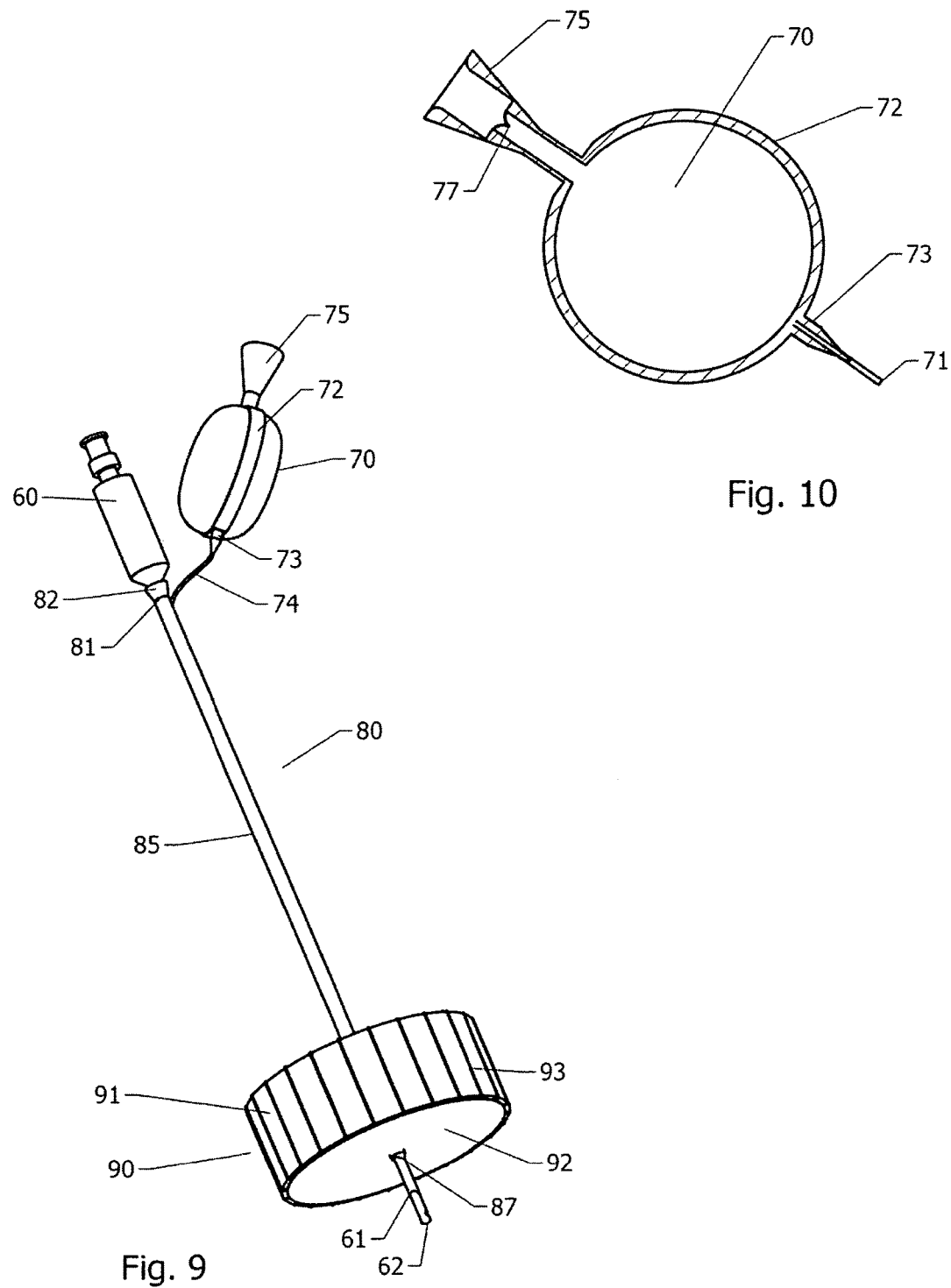
Figure 12:
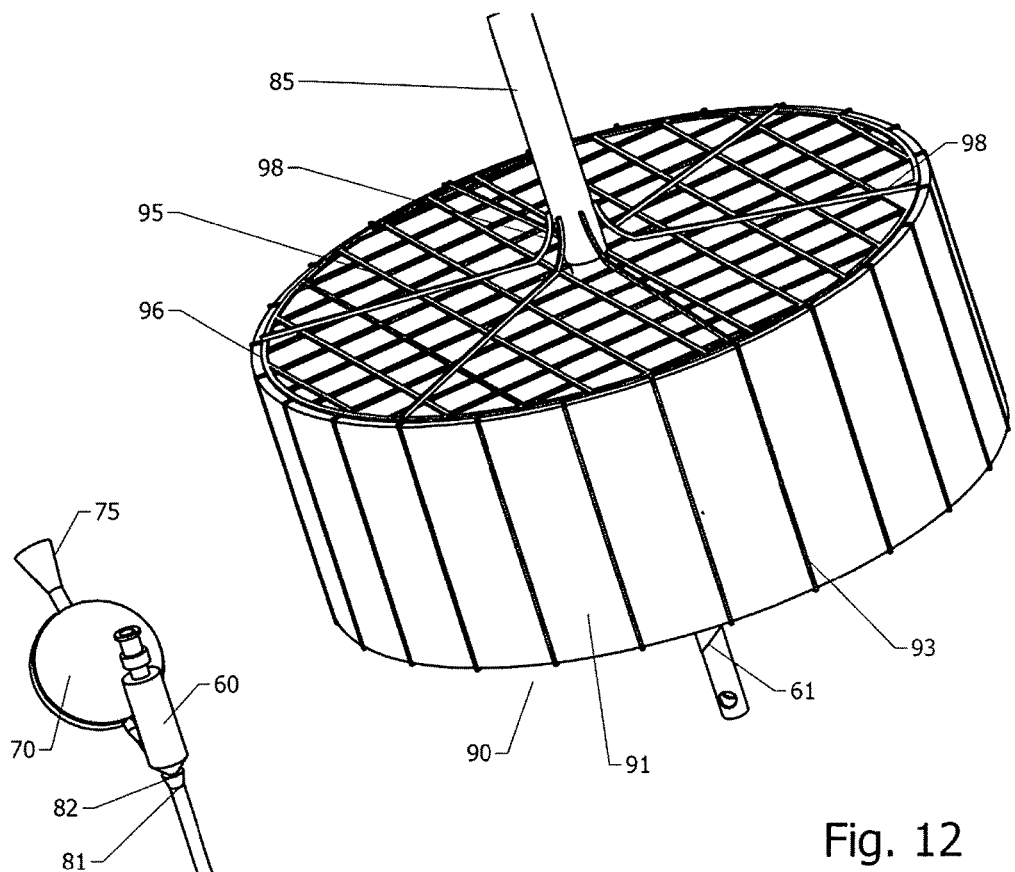
Figure 11:
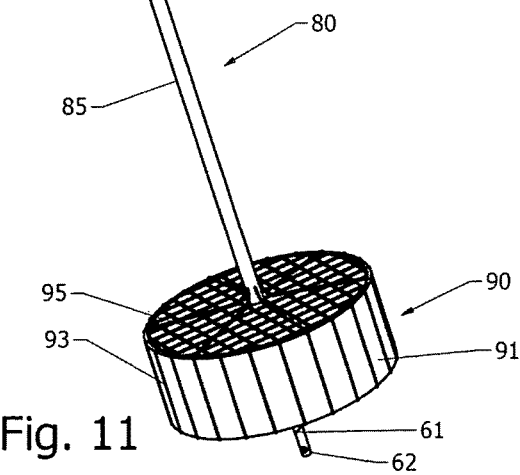

The puncture assistance device 10 comprises a tenaculum-like clamp 50, that is removably attached to the elongated body of the needle guide 15, this being also removably attached to the upper body of the ultrasound probe 5 by means of clamping fasteners 30 and 40 that fit closely around the handle part 6, respectively the elongated shaft 7 of the ultrasound probe and an elongated ridge 16 (FIG. 3) that fits within the elongated niche 8 of the ultrasound probe. The distal part of the body of the needle guide 15 presents a prominent part 20, which includes an inner slot for the insertion of the Veress needle 60.

The tenaculum clamp 50 is made of two opposing mirroring handles 51 and 52 with proximal finger loops, and two half-toroid segments 53 and 54 each one corresponding to a handle, that serve as pivot point, these being internally circumscribed by a circular ring 55 that is C-shaped on section and is holding segments 53 and 54 in contact to each other (FIG. 8). The handles 51, 52 are provided with ratchet fixation 56 at the level of the finger loops, represented by a series of interlocking teeth, a few on each handle, and the clamp also provides sharp incurving, needle-like inward pointing, sharp pointed curved blades 58 at the distal end.

Part 20 of the elongated body of the needle guide 15 also presents attachment means to the aforementioned clamp 50, which are represented by self-locking snap fit joints 17 and 17', that address the clamp's handles 51, 52 of round shape on section, as well as snap fit coupling assembly 23, which fits within the circular ring 55 of the clamp 50 when attached. Snap-fit coupling assembly 23 is located at the distal part of needle guide 15 on its upper face, and comprises two symmetrical solid prominences 24, 25 having the shape of a frustum of a cone segment located on top of a corresponding cylinder segment, together forming a base of rounded shape for inserting the circular ring 55 of clamp 50. The two segments 24, 25 are separated by a latching device represented by a non-permanent releasing cantilever snap 26 having knobs 27 of triangular shape on section that are attached to the base by flexible lamellas. The attachment of the clamp 50 to the needle guide 15 is made by pressing the clamp at the level of the circular ring 55 against the coupling assembly 23, thereby causing the knobs 27 to be pressed against each other in order to allow ring 55 to enter and be latched. The height of the coupling assembly 23 is slightly higher than the one of the pivot part of clamp 50, allowing thereby a slight tilting freedom of motion. Supplemental stability to the attachment is given by the following insertion of the clamp handles 51, 52 inside the snap fit joints 17 and 17', this step being optional. The detachment of the clamp 50 from the needle guide 15 is made by exerting angular traction on the handles 51, 52 at the level of their finger loops, which allows them to exit snap fit joints 17, 17', followed by manually squeezing together the knobs 27 this allowing ring 55 to exit the snap fit 23.

FIG. 3-8 illustrate the puncture assistance device 10 depicting several supplemental aspects thereof.

FIG. 5 depicts a cross section front view of the puncture assistance device made at the level of snap fit joints 17, 17'.

FIGS. 6 and 7 illustrate a cross section rear view of the puncture assistance device made at the level of clamping member 40 that addresses the elongated shaft 7 of the ultrasound probe.

The snap-fit joints 17, 17' (FIG. 5) are located on lateral protrusions 18, 18' of the prominent part 20 of the needle guide 15. Thereon arciform flexible lamellas 19, 19' partially include handles 51, 52, latching them in position when inserted.

The prominent part 20 of the needle guide 15 presents a sloped part 21 proximally from snap fit coupling assembly 23, that is including an inner slot 14 for the insertion of the Veress needle 60, this slot presenting an entry orifice 11 on the proximal face 22 of part 21, and an exit orifice 12 located at the distal tip of guide 15. The axis of slot 14 presents an angle in relation to the axis of the body of the needle guide, this angle allowing proper and easy manipulation of the Veress needle.

Clamping fastener 40 of needle guide 15 (FIG. 6, 7) is having an overall rounded shape that is correspondent to the shape on transversal section of the elongated shaft 7 that is flat on its upper side, comprising two symmetrical arciform lamellas 41, 42 that present an inferior opening in between that allows the insertion of shaft 7. Arciform lamellas 41, 42 thicken towards their ending into a cuboid shape with parallel inner and outer faces. At this point, the lamellas present orifice 45 on lamella 41 and 45' on lamella 42, through which a bolted screw 46 is inserted, this comprising an outer knob 47, that can be manually rotated, located outside orifice 45, from which a pin extension enters through slot 45 and ends into a threaded bolt 48, that enters the nut 49, located in orifice 45' of lamella 42. The bolt 48 presents a slight bigger diameter than the pin segment. Orifice 45 of lamella 41 presents an inner flange 44, which prevents bolt 48 from exiting the orifice when in retracted position.

The attachment of the ultrasound probe 5 to the needle guide 15 at this level is made by inserting the elongated shaft 7 through the opening between lamellas 41 and 42 with bolted screws in retracted position (FIG. 7), followed by pushing the bolt 46 towards orifice 45' of lamella 42, and screwing it into nut 49, thereby causing lamellas 41, 42 to approach each other, pressing within clamp 40 the shaft 7 of the ultrasound probe, hence resulting a solid grip at this level. The detachment of the ultrasound probe follows the same pathway in reverse order. Clamp fastener 30, located proximally presents a similar construction manner to clamp 40, the only difference being represented by the overall ovoid shape that addresses the handle section 6 of the ultrasound probe.

The attachment of the ultrasound probe 5 to the needle guide 15 is made by aligning them against each other, inserting handle 6 into clamp 30, elongated shaft 7 into clamp 40, and elongated ridge of needle guide 15 into corresponding niche 8, verifying the alignment, followed by the fastening of clamping members 30 and 40 until obtaining a solid grip.

FIG. 9-12 display a balloon retractor catheter 80 that serves as an external sheath of the Veress needle 60 upon entry. The balloon retractor catheter 80 comprises an elongated double lumen shaft 85, the length of which being inferior to that of the Veress needle shaft. Shaft 85 consists of two lumens, one being designated for the insertion of the Veress needle, the tip 61 surpassing the tip 87 of shaft 85 distally. The tip 87 is also sharpened in form of a needle tip, thereby easing the insertion of the balloon retractor catheter through the layers of the abdominal wall on the path created by the Veress needle 60. At the proximal end, the shaft 85 presents a neck 81 followed by a thickened adaptor 82 for the insertion of the Veress needle 60. The second lumen of the shaft 85 having a smaller diameter is represented by a channel there trough to pass a fluid between pilot balloon 70 and balloon retractor 90. The inflatable pilot balloon 70 presents a rounded shape, being made of resilient material, being included within a rigid frame 72, that comprises distally a protrusion 73 for the exit of tube 71, and proximally a female syringe connector 75, that presents a single direction flow valve 77, which doesn't allow the fluid entering the pilot balloon to exit it, except through tube 71, which connects the pilot balloon to the aforementioned second lumen of the elongated shaft 85. Tube 71 is surrounded by a flexible reinforcing, strengthened outer tube 74, which is inserted at the level of the neck 81 of the elongated shaft 85, surrounding it, assuring thereby that a strong pull may be exerted by hand by the operator.

Balloon retractor 90 is having an overall cylindrical shape, surrounding symmetrically the elongated shaft 85 to which it is attached on its inner side, and being surpassed distally by tip 87, being comprised of a balloon 91 represented by an inner layer of thin material, that when inflated recreates the aforementioned cylindrical shape, and is not inflatable beyond its maximum volume capacity. An outer mesh of reinforced, non-distendable thin fibers is attached to the outer surface of balloon 91, presenting different patterns on the different faces of cylinder. On its lower distal face, there is represented a single reinforced non-pierceable layer 92, that is attached on the outer surface of balloon 91. The lateral aspect of the fibers is represented by longitudinally oriented fibers 93, displayed in a circular pattern around balloon 90, connecting the lower, distal part 92 to the mesh 95 of the upper face. On the upper proximal side of the balloon 91, and attached to it, a cobweb-like net 95 of intersecting, interconnected fibers displayed in a crisscross pattern, creating non-distendable reinforced mesh spaces, with diameter significantly smaller than that of a trocar, but large enough for the sharp tip of the trocar to pass through. A trocar (FIG. 17) is a sharp pointed surgical instrument, which is used inside a hollow cannula to introduce it inside the abdomen in laparoscopic surgery. It is displayed as a means for introduction of cameras or other laparoscopic instruments. Net 95 is attached to and surrounded by circular fibers 96, which are being attached to longitudinal fibers 93, previously described, and also to radially ascending fibers 98 displayed in a circular pattern around shaft 85. Fibers 98 are connected to circular fibers 96, and ascend freely towards shaft 85, where they attach at a more proximal level than the level of mesh 95. The length of fibers 98 is equal or greater than the sum of the radius of cylinder 90 plus the distance between the upper face of cylinder 90 and the attachment level of fibers 98 onto shaft 85.

Upon insertion into the abdominal cavity, the balloon retractor 90 is inserted in deflated state, adjacent to the elongated shaft 85, to which the inner part of the balloon 91 is closely attached, with reinforced layer 92 on the outer side of the deflated complex of the balloon retractor.

FIG. 13-17 illustrate an abdominal entry technique in patients at risk for abdominal wall adhesion with the use of the aforementioned device.

Figure 13:
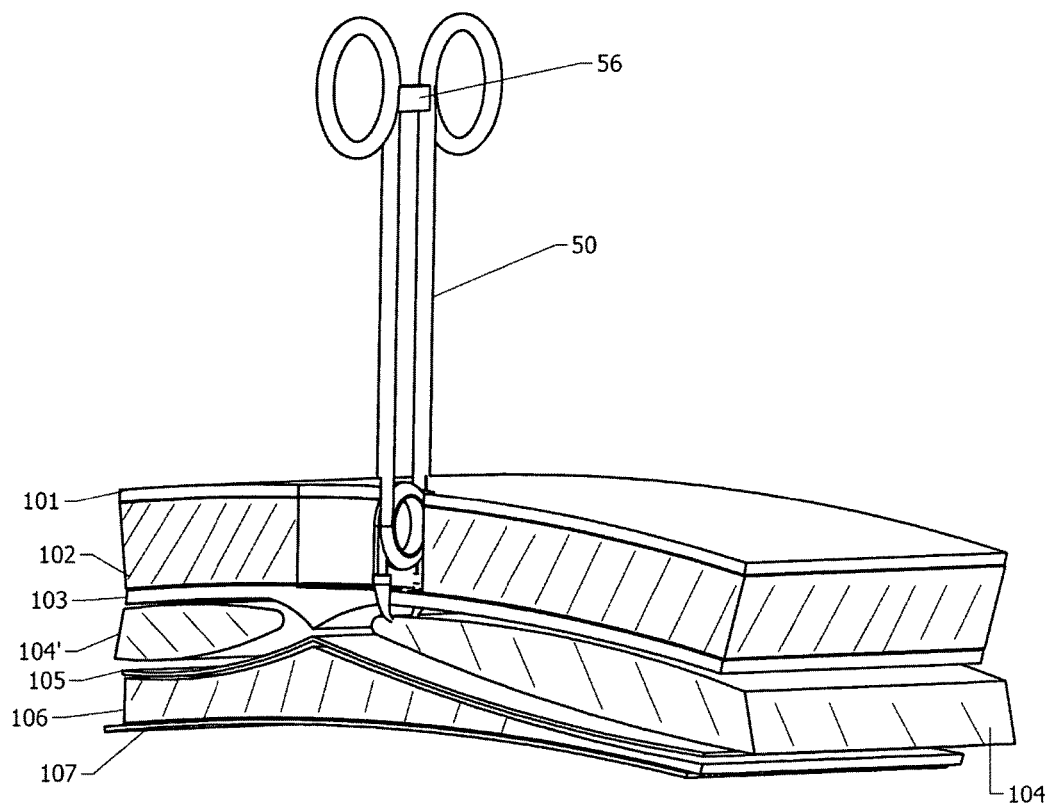

FIG. 13: A segment of the abdominal wall from the central area is depicted, the umbilicus being known to be the site of choice for primary entry in the abdomen by Veress needle or trocar. The following layers of the abdominal wall are represented: skin 101, subcutaneous fat tissue 102, anterior rectus fascia 103, body of the left 104 and right 104' rectus muscle, *transversalis* fascia 105, properitoneal fat 106, parietal peritoneum 107.

The first step is to create a small intra- or periumbilical incision of the skin 101 by scalpel, followed by the instrumental sharp and blunt dissection and retraction of the subcutaneous fatty tissue 102 to expose the fascia 103. After visualization of the fascia 103, this is grasped with tenaculum-like clamp 50 by piercing it with its sharp pointed hooks 58, and by securing the ratchet 56, resulting a solid grip at this level.

Figure 14:
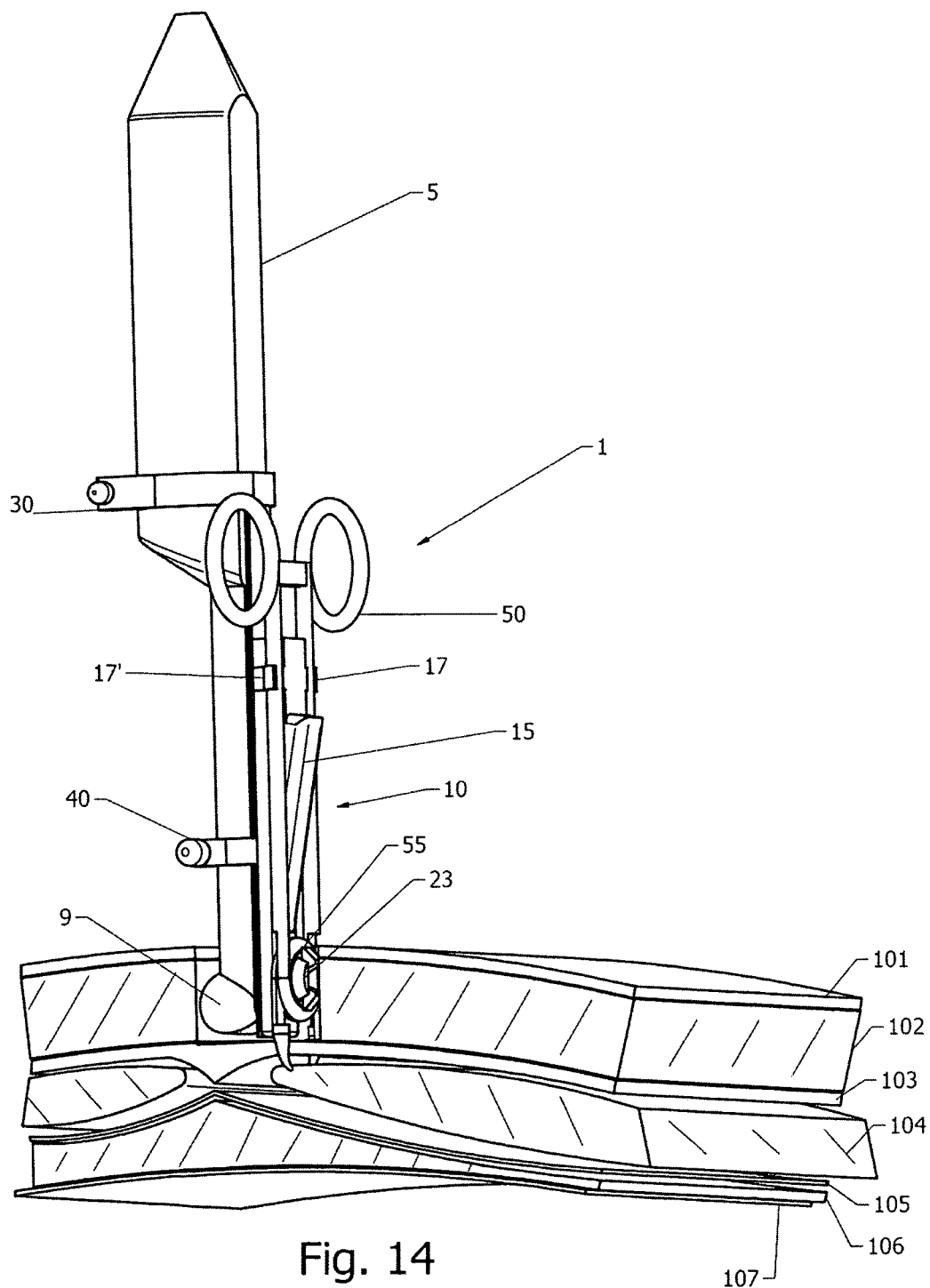

FIG. 14: The next step is to attach the ultrasound probe 5 to the needle guide 15 by fixing it with clamp fasteners 30 and 40, to align the resulted combination to clamp 50, and to attach the clamp 50 to the needle guide 15 by fastening coupling assembly 23 to the circular ring 55 and clamps handles to snap-fit joints 17, 17'. The scanning part 9 of the ultrasound probe and the tip of the needle guide are hereby in perpendicular contact to the fascia and attached to it by means of the clamp 50. The operator can hereby visualize on the desktop (not shown) of the ultrasound device the different layers of the abdominal wall, measure them, and apply pressure and traction on it, viewing the way that the layers are distended or compressed and especially the mobility of the inner organs, represented in this area by intestines and omentum in relation to the parietal peritoneum identifying thereby possible adhesions if the mobility is very limited.

A Doppler ultrasound of the abdominal wall helps identifying blood vessels that lay on the path of the instruments, and could be damaged. The path can therefore be changed by tilting or repositioning assembly 1.

At this point a visceral slide test and a peroperative periumbilical ultrasound-guided saline infusion test with a spinal needle through the slot of the needle guide 15 can be made by the aforementioned technique in order to identify possible occluding adhesions to the abdominal wall.

If these are identified, the operator can choose either:
to continue at this site and perform the safety tests and procedures that are to be described,
to tilt the complex formed by the puncture assistance device 10 and the ultrasound probe 5 for attempting entry at a different angle,
reposition the puncture assistance device—detach the needle guide 15 together with ultrasound probe 5 from tenaculum 50 and tenaculum from fascia 103, and to apply the same steps previously described at another level in the same incision
to leave this surgical site and continue at another site.

In thin patients it is possible to perform the aforementioned procedure and tests without performing an incision, by applying the tenaculum clamp 50 directly on the skin.

Figure 15:
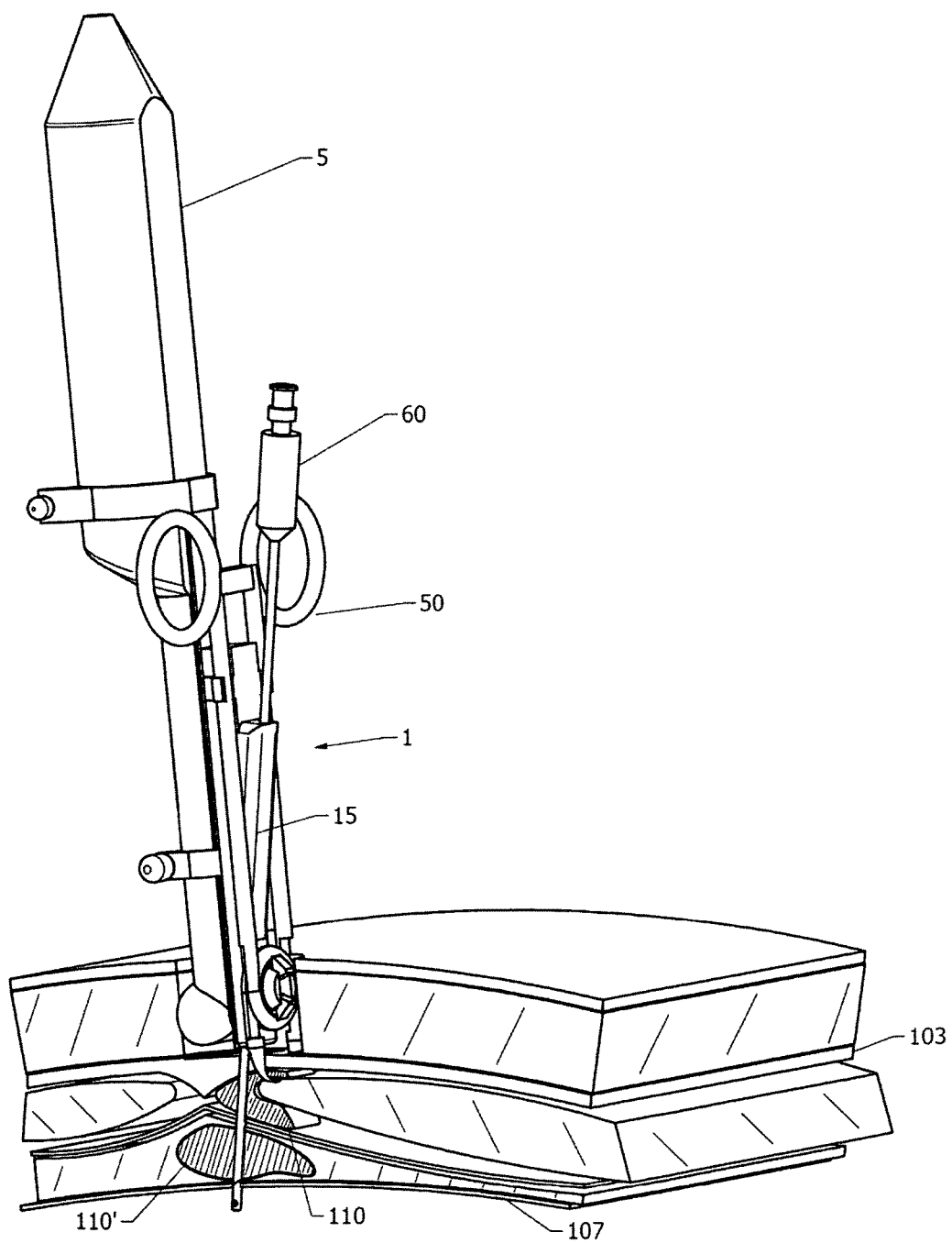

FIG. 15 illustrates the next step of using the assembly 1 that is applied on the rectus fascia 103, with the Veress needle 60 inserted through the needle guide 15 and pushed through the layers of the abdominal wall. One hand of the surgeon is gripping assembly 1, applying traction, while the other hand is inserting the Veress needle through the needle guide 15. The first assistant is holding a syringe with isotone solution that is coupled to the Veress needle by means of a connector (not seen). By applying traction on the rectus fascia by pulling assembly 1, the abdominal wall is pulled away from the inner organs and great retroperitoneal vessels, creating a space in between, and the different layers of the abdominal wall are spaced apart for a better differentiation on ultrasound. The path of insertion of the Veress needle 60 is displayed on the screen of the ultrasound device, until the perforation of the parietal peritoneum 107 and entrance into the abdominal cavity.

A clearer picture on the ultrasound can be obtained by infiltrating saline solution through the Veress needle while inserting it, hereby creating by hydro-dissection fluid pockets 110, 110' between the different layers of the wall that are separating them.

Of utmost importance is the fluid pocket 110' located in the properitoneal layer 106, as this allows the precise measurement of the peritoneal membrane 107, whose thickness differs with age and associated pathology, and the relation between inner organs (represented at this level by intestine and omentum) and the peritoneal membrane depicting either mobility or immobility of the underlying structures.

A measurement corresponding to the normal thickness of the peritoneum 107 according to age and pathology associated with normal motion of the underlying structures when mobilizing the abdominal wall by pushing/pulling it with assembly 1 should exclude the presence of occluding parietal adhesions and ensure a safe entry at the site, followed by piercing the peritoneal membrane with the Veress needle.

An abnormally thickened peritoneal membrane with an inhomogeneous structure that cannot be distinguished from the underlying structures, which are relative immobile to the abdominal wall, raises the suspicion for occluding adhesions. In this case, the operator can choose either:

to tilt the complex formed by the assembly 1 for attempting entry at a different angle, continuing with hydrodissection until normal peritoneum and underlying mobility are depicted, to reposition the puncture assistance device—detach the needle guide 15 together with ultrasound probe 5 from tenaculum 50 and tenaculum from fascia 103, and to apply the same steps previously described at another level in the same incision, to leave this surgical site and continue at another site.

After piercing the peritoneum and entering the abdominal cavity, one should continue the instillation of fluid. Normally the fluid disappears as instilled as it flows in the cavity. If fluid pockets are depicted that do not disappear, occlusive adhesions are to be suspected.

After ensuring the safe entry into the abdominal cavity, the Veress needle is connected to the insufflation tubing and the abdomen is inflated with $CO_2$.

Assembly 1 should not be discarded while insufflating the pneumoperitoneum, as occult adhesions may become obvious at this time, interfering and creating supplemental risk when inserting the trocar. Normally with insufflation the intraabdominal structures underlying the peritoneum disappear from the screen of the ultrasound device, as gas is non-conductive to ultrasound waves. When observing intraabdominal structures that remain adherent to the abdominal wall and elevate together with it when insufflating, occlusive adhesions are present that may be damaged upon first trocar insertion.

Figure 16:
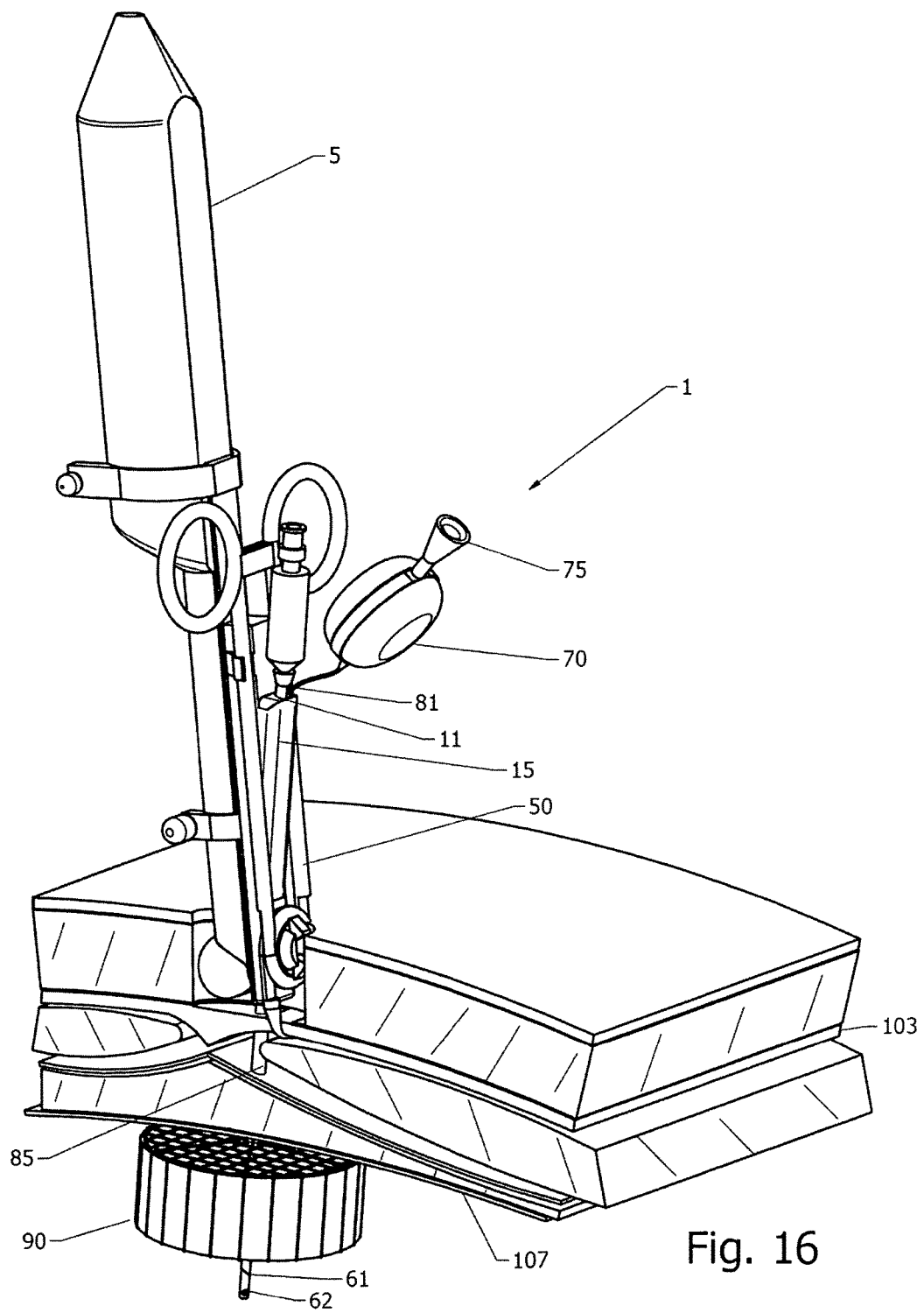

FIG. 16 illustrates an alternative way of entry by using the balloon retractor catheter 80 in conjunction and as an external sheath to the Veress needle 60. Insertion steps and safety tests are the same as previously described, with balloon 90 in deflated state, applied to the body of the elongated shaft (not shown). After ensuring safe entry into the abdominal cavity, the Veress needle 60 and the balloon catheter 80 are pushed through until the neck 81 engages the slot of the puncture assistance device 10 at the level of orifice 11. A fluid filled syringe is then adapted to the female syringe connector 75 of the pilot balloon 70 and liquid is instilled hereby. The balloon 90 is filled with fluid until its maximum volume capacity where it assumes the cylindrical shape previously described, and any loose adhesions are pushed aside. The filling of the balloon 90 is witnessed by the inflation of the pilot balloon 70, without being followed by deflation as the latter is manufactured of elastic material, the connector 75 presenting a unidirectional valve, which allows only filling. By pulling on the pilot balloon 70, the upper face of the balloon 90 is applied on the inner surface of the peritoneum 107. This can be visually confirmed by identifying the fluid filled balloon in position on the screen of the ultrasound device. At this time, any thickening between the peritoneum and the upper face of the balloon retractor can be considered an adhesion, and that path should be avoided when inserting the primary trocar, except for when it disappears when the balloon is pushed inward and retracted afterwards.

Figure 17:
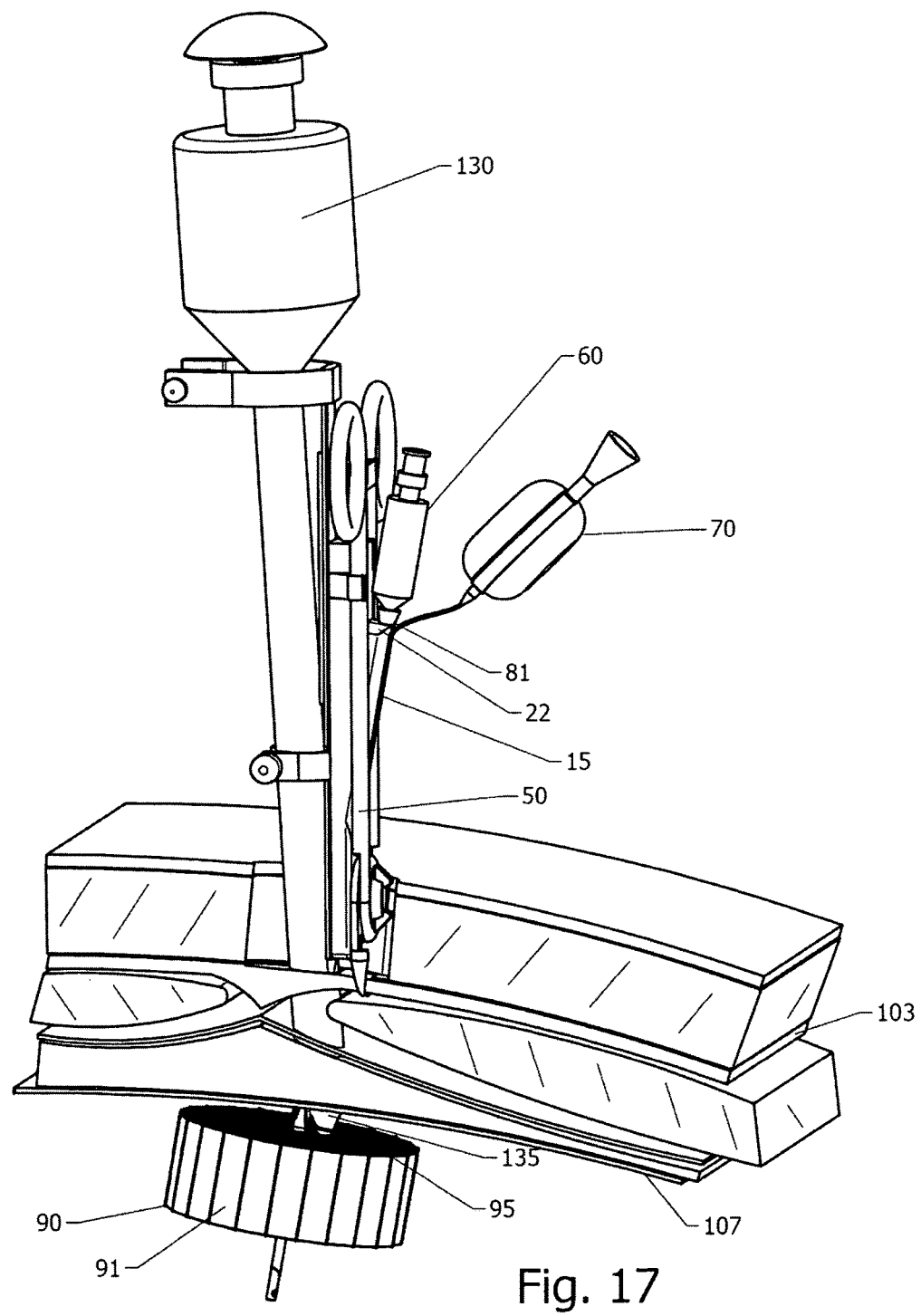

FIG. 17 illustrates the entry of the primary trocar by using this technique. After ensuring the safety of entry by the aforementioned methods, the ultrasound probe 5 is uncoupled from puncture assistance device 10 and removed, and a trocar 130 is inserted through the skin incision to impact the fascia 103, at a small distance to the level where Veress needle 60 and balloon catheter 80 pierce the fascia and with a similar orientation. Rotating advancing movement are exerted on the trocar with one hand while the other provides counter-traction on the pilot balloon 70, lifting thereby the abdominal wall and ensuring close contact between the upper face of the cylindrical balloon 90 and the parietal peritoneum 107. As the sharp tip 135 of the trocar enters the abdominal cavity through the peritoneum, it will come in contact with the balloon retractor 90. It will enter through the mesh 95, and pierce the thin wall of balloon 91, creating a hole in it and causing it to burst, followed by the collapse of the mesh 95 around the tip of the trocar. This is witnessed by the rapid deflation of the elastic pilot balloon 70, which empties its content into the abdominal cavity through the burst balloon. As mentioned, tip 135 of the trocar enters in one of the non-distendable mesh holes of 95, of smaller diameter than the trocar, being entangled in it, and contacts the inferior reinforced layer 92 that it cannot pierce. The previously described radially ascending fibers 98 (FIG. 12) prevent the lateral misplacement of the mesh 95 after the collapse of the balloon 91, by keeping the surrounding circular fibers 96 in a steady position, creating a hammock-like stable structure that induces a centralized path to the trocar towards layer 92, and does not allow it to slip sideways. After the deflation of the pilot balloon 70, one should exert a lower amount of counter-traction at its level and let the balloon slide together with the trocar for a small distance until the insertion of the cannula, as layer 92 will prevent possible damage made by the sharp tip of the trocar. After the insertion of the cannula through the abdominal wall, the sharp trocar is removed, releasing thereby the collapsed balloon 90. The removal of the balloon 90 is made by pulling it reversely through its path after removing clamp 50 from the fascia, and disassembling it from needle guide 15, by traction exerted on the needle guide 15, which impacts at the level of slot orifice 11 of face 22 the neck 81 of the balloon trocar 85.

Figure 18:
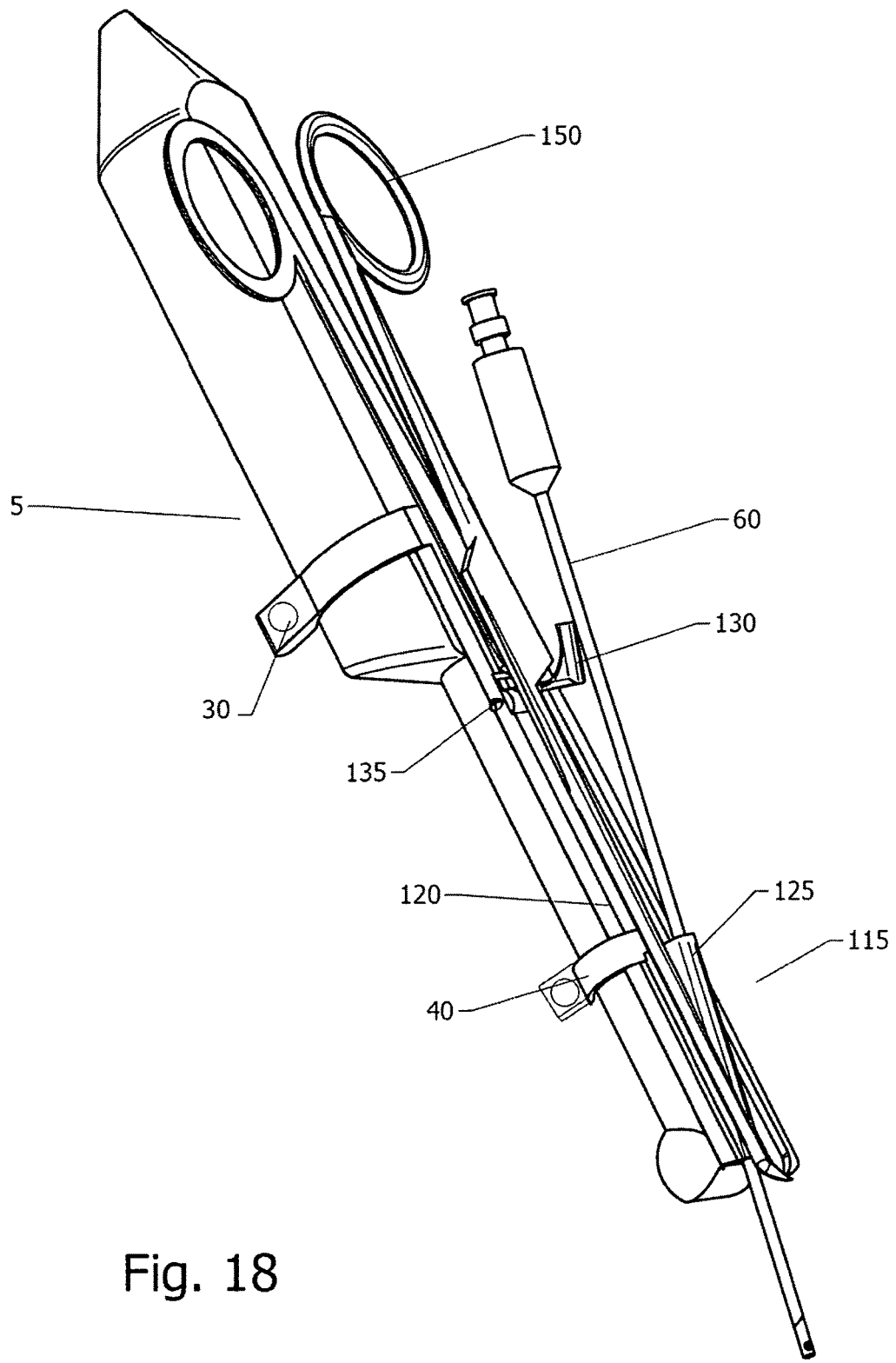

FIG. 18 introduces an alternate embodiment of the invention, namely assembly 110, which comprises ultrasound probe 5, attached to needle guide assembly 115 that contains tenaculum 150 and needle guide 120. Through a slot in the prominent part 125 of the needle guide 120, a Veress needle 60 is inserted. Attachment of the puncturing assistance device to the ultrasound probe is made by similar means as in the former embodiment by clamps 30, 40. Attachment of the tenaculum 150 to the needle guide 120 is made by lever 130 that rotates around pivot 135, inserted at the level of the elongated base of needle guide 120. Lever 130, is presenting an L-shape that allows it to be elevated from the base by pulling on the shorter segment, and insert it between the handles of the tenaculum 150, securing it thereby to the needle guide 120.

What is claimed is:

1. A method to access a body cavity under ultrasound guidance comprising:

providing a balloon retractor with an inflatable balloon partially covered by a non-distendable mesh, an ultrasound probe, a puncture assistance device connected to attachment means for attaching said puncture assistance device to a wall of said cavity, and a needle, the puncture assistance device being operably connected to said ultrasound probe;

securing said attachment means to a component of said cavity wall;

inserting said needle through said puncture assistance device;

directing a path of the needle until entering said cavity according to information provided by the ultrasound probe, while manipulating said wall through said attachment means;

inserting said balloon retractor with said balloon in a collapsed state into said cavity guided by said needle;

inflating the balloon, thereby expanding said non-distendable mesh and pulling said balloon retractor against the cavity wall under ultrasound vision;

applying traction on said balloon retractor while inserting a sharp trocar against said balloon retractor through said cavity wall, whereby said non-distendable mesh catches the sharp tip of said trocar when entering said bodily cavity, preventing organ injuries.

2. The method of claim 1, whereby said cavity is represented by an abdominal cavity, and said attachment means is represented by sharp hooks of tenaculum forceps attached on the abdominal cavity.

3. The method of claim 1, whereby said cavity is represented by an abdominal cavity, and said attachment means is represented by sharp hooks of a tenaculum forceps attached on a uterine cervix.

4. The method of claim 1, whereby said cavity is represented by a hollow inner organ.

5. The method of claim 1, whereby a fluid is injected through said needle for creation of fluid pockets that provide a better ultrasound image, allowing for measuring a thickness of a peritoneal membrane.

6. The method of claim 1, that further comprises providing said balloon retractor with a pilot balloon that marks the piercing of said balloon by said trocar by rapid deflation.

7. A method to gain access to a body cavity with a trocar having a sharp tip, the method comprising:

providing a balloon retractor with an inflatable balloon partially covered by a non-distendable mesh;

inserting said balloon retractor with said balloon in a collapsed state into said cavity guided by a Veress needle;

inflating the balloon thereby expanding said non-distendable mesh and pulling said balloon retractor against the cavity wall; and applying traction on said balloon retractor while inserting the trocar against said balloon retractor through said cavity wall, whereby said non-distendable mesh catches the sharp tip of said trocar when entering said cavity, thereby preventing organ injuries.

8. The method of claim 7 further comprising providing said balloon retractor with a pilot balloon that marks the piercing of said balloon by said trocar by rapid deflation.

* * * * *